United States Patent [19]

Wallace et al.

[11] Patent Number: 5,639,611
[45] Date of Patent: Jun. 17, 1997

[54] ALLELE SPECIFIC POLYMERASE CHAIN REACTION

[75] Inventors: R. Bruce Wallace, Greenbrae; Bijay K. Pal, Arcadia; Luis A. Ugozzoli, San Rafael, all of Calif.; Dan Y. Wu, Bellevue, Wash.

[73] Assignee: City of Hope, Duarte, Calif.

[21] Appl. No.: 338,217

[22] Filed: Nov. 9, 1994

Related U.S. Application Data

[63] Continuation of Ser. No. 852,031, Apr. 1, 1991, abandoned, which is a continuation of Ser. No. 283,142, Dec. 12, 1988, abandoned.

[51] Int. Cl.⁶ .................. C12P 19/34; C12Q 1/68
[52] U.S. Cl. .................. 435/6; 435/91.2; 935/77; 935/78
[58] Field of Search ............ 435/6, 91.2; 935/77, 935/78

[56] References Cited

U.S. PATENT DOCUMENTS

| | | | |
|---|---|---|---|
| 4,656,127 | 4/1987 | Mundy | 435/6 |
| 4,683,195 | 7/1987 | Mullis et al. | 435/6 |
| 4,820,630 | 4/1989 | Taub | 435/6 |
| 4,851,331 | 7/1989 | Vary et al. | 435/6 |
| 4,965,188 | 10/1990 | Mullis et al. | 435/6 |

OTHER PUBLICATIONS

Gyllensten et al., PNAS (USA) 85:7652–7656 (Oct., 1988).
Conner et al. PNAS (USA) 80:278–282 (1983).
Saiki et al. Nature 324:163–166 (1986).
Wu, D.Y., et al., "Allele–specific enzymatic amplification of b–globin genomic DNA for diagnosis of sickle cell anemia" *Proc. Natl. Acad.Sci. USA* 86:2757–2760 (1989).
Battula, N., et al., "Lack of Exodeoxyribonuclease Activity and Error–Correcting Function in Avian Myeloblastosis Virus DNA Polymerase", *J. Biol. Chemistry* 251(4):982–986 (1976).

Tabor, S., et al., "Selective oxidation of the Exonuclease Domain of Bacteriophage T7 DNA Polymerase", *J. Biol. Chemistry* 262(32):15330–15333 (1987).
Tabor, S., et al., "Selective Inactivation of the Exonuclease Activity of Bacteriophage T7 DNA Polymerase by in Vitro Mutagenesis", *J. Biol. Chemistry* 264(11):6447–6458 (1989).
Kleppe, K., et al., "Repair Replication of Short Synthetic DNA's as catalyzed by DNA Polymerases", *J. Mol. Biol.* 56:341–361 (1971).
Kornberg, A., "Active Center of DNA Polymerase", *Science* 163:1410–1418 (1969).
Kornberg, A., "DNA REplication" (San Francisco: W.H. Freeman and Company) (1980) Table 10–2 only.
Tindall, K.R., et al., "Fideltiy of DNA Synthesis by the Thermus aquaticus DNA Polymerase", *Biochemistry* 27(16):6008–6013 (1988).
Klenow, H., et al., "Selective Elimination of the Exonuclease Activity of the Deoxyribonucleic Acid Polymerase from *Escherichia coli* B by Limited Proteolysis", *Proc. Natl. Acad. Sci.* 65(2):168–175 (1970).
Derbyshire, V., et al., "Genetic and Crystallographic Stuides of the 3',5'–Exonucleolytic Site of DNA Polymerase" *Science* 240:199–201 (1988).

*Primary Examiner*—Stephanie W. Zitomer
*Attorney, Agent, or Firm*—Rothwell, Figg, Ernst & Kurz

[57] ABSTRACT

A rapid, non-radioactive approach to the diagnosis of sickle cell anemia is described based on an allele specific polymerase chain reaction (ASPCR) in which the 3'-terminal nucleotide of one of the primers of the primer set forms a match with one allele and a mismatch with the other allele. This method allows the direct detection of the normal or the sickle cell β-globin allele in genomic DNA without the additional steps of probe hybridization, ligation or restriction enzyme cleavage.

4 Claims, 3 Drawing Sheets

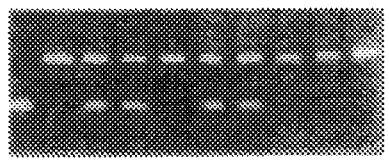
FIG. 2A
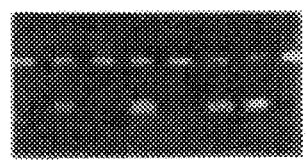
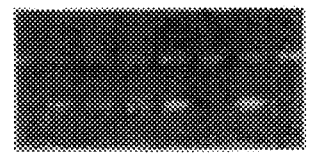
FIG. 2B
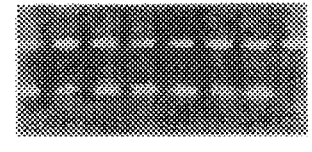

ALLELE SPECIFIC POLYMERASE CHAIN REACTION

This application is a continuation of (fwc) of now abandoned application Ser. No. 07/852,031 filed Apr. 1, 1991 which is a continuation (fwc) of non abandoned application Ser. No. 07/283,142 filed Dec. 12, 1988.

FIELD OF INVENTION

This invention entails an allele specific polymerase chain reaction (ASPCR) useful, inter alia, for the direct detection of the normal or the sickle cell β-globin in genomic DNA without the additional steps of probe hybridization, ligation or restriction enzyme cleavage.

BACKGROUND

Sickle cell anemia is the paradigm of a genetic disease caused by a single base-pair mutation, an A→T transversion in the sequence encoding codon 6 of the human β-globin gene. In homozygous sickle cell anemia, the substitution of a single amino acid (Glu→Val) in the β-globin subunit of hemoglobin results in a reduced solubility of the deoxyhemoglobin molecule, and red blood cells assume irregular shapes. The sickled red blood cells become trapped in the microcirculation and cause damage to multiple organs.

Kan and Dozy[1] were the first to describe the diagnosis of sickle cell anemia in the DNA of affected individuals based on the linkage of the sickle cell allele to an Hpa I restriction fragment length polymorphism. Later, it was shown that the mutation itself affected the cleavage site of both Dde I and Mst II and could be detected directly by restriction enzyme cleavage.[2] Conner et al.[3] described a more general approach to the direct detection of single nucleotide variation by the use of allele specific oligonucleotide hybridization. In this method, a short synthetic oligonucleotide probe specific for one allele only hybridizes to that allele and not to others under appropriate conditions.

1 Kan, Y. W., et al., *Lancet* 2:910–912 (1978).
2 Geever, R. F., et al., *Proc. Natl. Acad. Sci. USA* 78:5081–5085 (1982); Chang, J. C., et al., *N. Engl. J. Med.* 307:30–32 (1982).
3 Conner, B. J., et al., *Proc. Natl. Acad. Sci. USA* 80:278–282 (1983).

All of the above approaches are technically challenging, require a reasonably large amount of DNA and are not very rapid. The polymerase chain reaction (PCR) developed by Saiki, et al.[4] provided a method to rapidly amplify small amount of a particular target DNA. The amplified DNA could then be readily analyzed for the presence of DNA sequence variation (e.g., the sickle cell mutation) by allele specific oligonucleotide hybridization,[5] restriction enzyme cleavage.[6] ligation of oligonucleotide pairs[7] or ligation amplification. PCR increased the speed of analysis and reduced the amount of DNA required for it, but did not change the method of analysis of DNA sequence variation.

4 Saiki, R. K., et al., *Science* 230:1350–1354 (1985).
5 Saiki, R. K., et al., *Nature* 324:163–166 (1986).
6 Saiki, R. K., et al., *Science* 230:1350–1354 (1985); Chehab, F. F., et al., *Nature* 329:293–294 (1987).
7 Landegren, U., et al., *Science* 241:1077–1080 (1988).

SUMMARY

PCR is conducted in an allele specific manner such that the presence or absence of an amplified fragment provides direct determination of genotype. Two allele specific oligonucleotide primers, one specific for the sickle cell or other mutant allele and one for the normal allele, together with another primer complementary to both alleles, are used in the PCR with genomic DNA templates. The allele specific primers differ from each other, for example, in their terminal 3' nucleotide. Under the primer annealing temperature and PCR conditions, these primers only direct amplification on their complementary allele. In a single blind study of DNA samples from 12 individuals, this method correctly and unambiguously allowed for the determination of the genotypes with no false negatives or positives. When combined with appropriate labeling techniques, this method promises to be a powerful approach for genetic disease diagnosis, carrier screening, HLA typing, human gene mapping, forensics and paternity testing.

DETAILED DESCRIPTION OF THE INVENTION

PCR utilizes two oligonucleotide primers that anneal to opposing strands of DNA at positions spanning a sequence of interest. A DNA polymerase (either the Klenow fragment of *E. coli* DNA polymerase I[8] or *Thermus aquaticus* DNA polymerase[9]) is used for sequential rounds of template dependent synthesis of the DNA sequence. Prior to the initiation of each new round, the DNA is denatured and fresh enzyme added in the case of the *E. coli* enzyme. In this manner, exponential amplification of the target sequences is achieved. If the 3' nucleotide of one of the primers formed a mismatched base-pair with template due to the existence of single nucleotide variation, amplification takes place with reduced efficiency. Specific primers thus direct amplification only from their homologous allele. After multiple rounds of amplification, the formation of an amplified fragment indicates the presence of the allele in the initial DNA.

8 Saiki, R. K., et al., *Science* 230:1350–1354 (1985).
9 Saiki, R. K., et al., *Science* 239:487–491 (1988).

DESCRIPTION OF THE FIGURES

FIG. 2 (A) illustrates identification of the normal ($\beta^A$) and the sickle cell ($\beta^S$) alleles by ASPCR. 0.5 µg of normal ($\beta^A/\beta^A$), homozygous sickle cell ($\beta^S/\beta^S$), homozygous sickle cell ($\beta^S/\beta^S$)), heterozygous sickle cell ($\beta^A/\beta^S$) and homozygous β-thalassemia ($\beta^{th}/\beta^{th}$) DNA samples served as template using either the normal (a primer set) or the sickle cell (s primer set) for the allele specific PCR reactions. As an internal positive control, all reactions contained an additional primer set for the human growth hormone gene (hGH primer set) which directed the amplification of a 422 bp fragment of the human growth hormone gene. After amplification, 15 µl from each reaction was subjected to electrophoresis in a 1.5% agarose gel for 2 hours at 120 V. Ethidium bromide staining of the agarose gel was used to detect PCR amplified fragments. Positive β-globin allele specific PCR can be identified by the presence of a 203 bp fragment using either the a or the s primer set reaction. As a marker for the globin specific fragment, 0.3 µg of plasmid pHβ⁴ containing the normal human globin gene ($\beta^A$) was amplified with the primer set alone (M1). As a marker for the growth hormone specific fragment, 0.1 µg of plasmid pXGH5 containing a 3.8 kb fragment of the human growth hormone gene[10] was amplified with the growth hormone primer set (hGH) alone (M2).

10 Selden, R. F., et al., *Mol. Cell Biol.* 6:3173–3179 (1986).

FIG. 2 (B) reflects a single blind trial using ASPCR to diagnose the β-globin genotype of genomic DNA samples. Genomic DNA samples from 12 individuals (four each of normal, homozygous and heterozygous sickle cell individuals) were randomly assigned numbers 1 to 12 by the hematology laboratory and blinded to the investigators. ASPCR was performed using both the normal (a) and the sickle cell (s) specific primer sets as described above. Genotypes were identified as homozygous normal ($\beta^A/\beta^A$) if the single 203 bp fragment appears exclusively in the a primer set reaction, as homozygous sickle cell ($\beta^S/\beta^S$) if the 203 bp fragment appears only in the s primer set, or as heterozygous sickle cell trait ($\beta^A/\beta^S$) if the fragment appears in both reactions. The genotypes of these DNA samples were previously determined by hemoglobin electrophoresis (results not shown). The genotypes of the 12 individuals are: 1,2,3,5—$\beta^A/\beta^A$; 6,9,10,11—$\beta^A/\beta^S$; 4,7,8,12—$\beta^S/\beta^S$.

Figure 3:
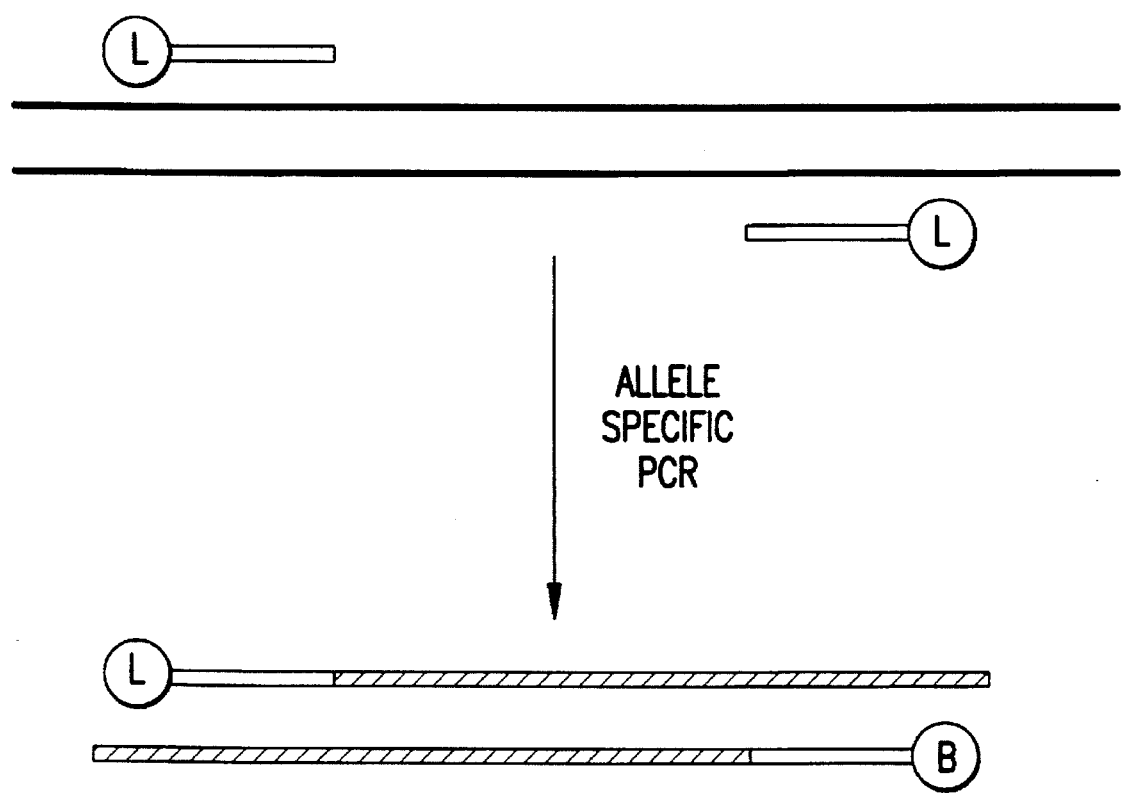

FIG. 3 is a schematic representation of a dual labeling system suitable for the detection of the ASPCR products. One of the oligonucleotide primers is labeled at the 5' end with a fluorescent group such as fluorescein or tetramethyl rhodamine (L) and the other primer is labeled with biotin (B). The ASPCR amplification product would therefore have the 5' end labeled on both strands. The biotin is suitable for capturing the amplified fragment on a streptavidin-agarose column while the fluorescent group is suitable for measuring the amount of fragment produced.

EXEMPLIFICATION OF THE INVENTION

Oligonucleotide synthesis

Oligonucleotides were synthesized on an Applied Biosystems 380B DNA synthesizer using the phosphoramidite method. They were purified by electrophoresis on a urea/polyacrylamide gel followed by high performance liquid chromatograph as described elsewhere.[11]

11 Dembek, P., et al., J. Am. Chem. Soc. 103:706-708 (1981).

Source and isolation of human DNA

Genomic DNA samples were isolated from the peripheral blood of appropriate individuals. The β-globin genotype of these individuals was previously determined by hybridization with allele specific oligonucleotide probes[12] as well as by hemoglobin electrophoresis. Thalassemia major DNA was obtained from an EBV-transformed lymphocyte cell line obtained from the NIGMS Human Genetic Mutant Cell Repository (Camden, N.J.). Thalassemia DNA was isolated from the cultured cells. All DNA preparations were performed according to a modified Triton X-100 procedure followed by Proteinase K and RNAse A treatment.[13] The average yield of genomic DNA was approximately 25 µg/ml of blood.

12 Conner, B. J., et al., Proc. Natl. Acad. Sci. USA 80:278-282 (1983).
13 Bell, G. I., et al., Proc. Natl. Acad. Sci. USA 78:5759-5763 (1981).

Polymerase Chain Reaction

Hβ14A (5' CACCTGACTCCTGA) and BGP2 (5' AATAGACCAATAGGCAGAG) at a concentration of 0.12 µM concentration were used as the primer set for the amplification of the normal β-globin gene (a primer set). Similarly, 0.12 µM each of Hβ14S (5= CACCTGACTCCTGT) and BGP2 were used as the primer set for the amplification of the sickle cell gene (s primer set). Both primer sets directed the amplification of a 203 bp β-globin allele specific fragment. As an internal positive control, all reactions contained an additional primer set for the human growth hormone gene comprised of 0.2 µM each of GHPCR1 (5' TTCCCAACCATTCCCTTA) and GHPCR 2 (5' GGATTTCTGTTGTGTTTC) (hGH primer set). GHPCR1 and GHPCR2 direct the amplification of a 422 bp fragment of the human growth hormone gene. All reactions were performed in a volume of 50 µl containing 50 mM KCl, 10 mM Tris-HCl (pH 8.3), 1.5 mMMgCl₂, 0.01% (w/v) gelatin, 0.5 µg/ml template DNA and 0.1 mM each of dATP, dCTP, dGTP, and dTTP. Reactions were carried out for 25 cycles at an annealing temperature of 55° C. for 2 min., a polymerization temperature of 72° C. for 3 min. and a heat denaturation temperature of 94° C. for 1 min. on a Perkin-Elmer-Cetus DNA Thermal Cycler. At the end of the 25 rounds, the samples were held at 4° C. in the thermal cycler until removed for analysis. The annealing temperature may be carried out at a temperature range from about 50° C. to about 70° C. and the polymerization step at a temperature of from about 85° C. to about 100° C.

Analysis of the PCR products

An aliquot (15 µl) of each of the completed PCR reaction was mixed with 5 µl of 5X Ficoll loading buffer (1X=10 mM Tris-HCl pH 7.5, 1 mM EDTA, 0.05% bromophenol blue, 0.05% Xylene cyanol and 3% Ficoll) and subjected to electrophoresis in a 1.5 agarose gel. Electrophoresis was performed in 89 mM Tris-HCl, 89 mM Borate, 2 mM EDTA buffer for 2 hours at 120 V. At the completion of electrophoresis, the gel was stained in 1.0 µg/ml ethidium bromide for 15 min., destained in water for 10 min., and photographed by ultra violet trans-illumination.

Experimental Design

Figure 1A:
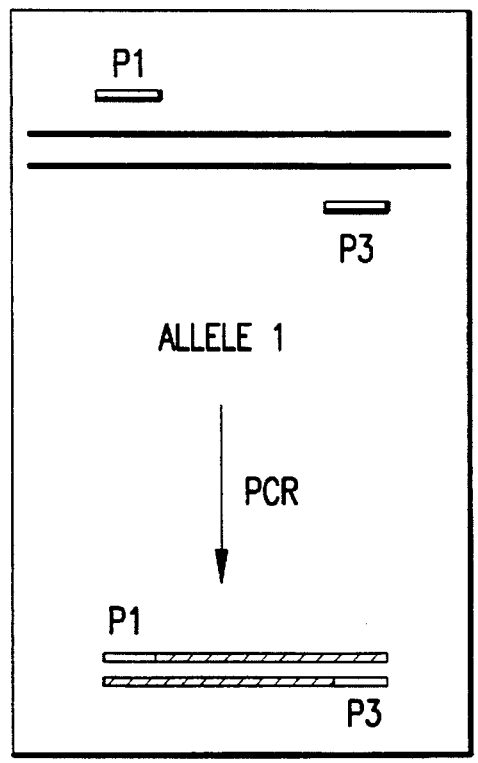
FIG. 1 is a schematic representation of the ASPCR. P1 and P3 are synthetic oligonucleotide primers that anneal to opposing strands of a single copy gene. P1 anneals to the region of a gene in the region of a DNA sequence variation such that its terminal 3' nucleotide base-pairs with the polymorphic nucleotide. P1 is completely complementary to allele 1 (A) but forms a single base-pair mismatch with allele 2 at the 3' terminal position due to one or more nucleotide differences relative to allele 1 (B).
Figure 1B:
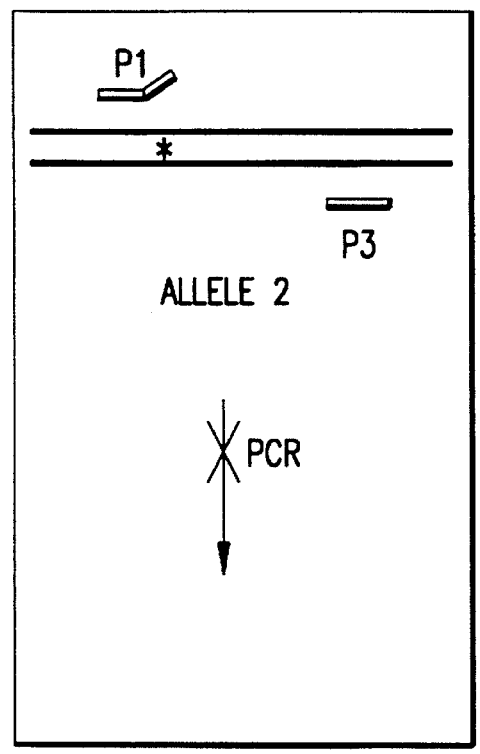

The scheme describing ASPCR is shown in FIG. 1. Primer P1 is designed such that it is completely complementary to allele 1 but the 3' terminal nucleotide forms a single base-pair mismatch with the DNA sequence of allele 2 (*). Under appropriate annealing temperature and PCR conditions, there is normal amplification of the P1-P3 fragment with DNA templates containing allele 1 (homo- or heterozygous) while there is little or no amplification from DNA templates containing allele 2. In a similar way, a primer (P2) could be designed which would allow the specific PCR amplification of allele 2 but not allele 1 DNA. Two 14 nucleotide long allele specific primers, Hβ14S and Hβ14A, complementary at the 5' end of the sickle cell and normal β-globin genes respectively were designed. The oligonucleotide primers differ from each other by a single nucleotide at the 3' end, Hβ14S having a 3' T and Hβ14A having a 3' A corresponding to the base-pair affected by the sickle cell mutation. The oligonucleotide primer BGP2 complementary to the opposite strand 3' of the allele specific primers was used as the second primer for PCR. The amplification product with these primer pairs was 203 bp. Also included in each reaction was a second pair of primers which directed the amplification of a 422 bp fragment of the human growth hormone gene. These primers were included as an internal positive control.

Detection of sickle cell allele

Genomic DNA was isolated from peripheral blood leukocytes of individuals of known β-globin genotypes ($\beta^A/\beta^A$, $\beta^A/\beta^S$, $\beta^S/\beta^S$). In addition, DNA was isolated from an EBV-transformed cell line containing a homozygous deletion of the β-globin gene ($\beta^{th}/\beta^{th}$). DNA was subjected to 25 rounds of PCR using either the sickle cell specific primer set (Hβ14S and BGP2) or the normal gene specific primer set (Hβ14A and BGP2) using an annealing temperature of 55° C. The results are shown in FIG. 2(A). A 203 bp fragment is observed using the sickle cell specific primer set only with the $\beta^A/\beta^S$ and $\beta^S/\beta^S$ genomic DNA templates and not with the $\beta^A/\beta^A$ genomic DNA templates. Conversely, the normal gene specific primer set only gave rise to an amplification product with $\beta^A/\beta^S$ and $\beta^A/\beta^A$ genomic DNA templates. The thalassemia DNA did not give rise to a β-globin gene amplification product with either primer set. The internal growth hormone gene control gave rise to a 422 bp fragment in all samples, demonstrating that in no case was the absence of a globin specific band due to a failure of the PCR.

In a single blind study, the DNA from 12 individuals with different β-globin genotypes was analyzed with the two primer sets. The results are shown in FIG. 2(B). Individuals 1,2,3 and 5 are predicted to be $\beta^A/\beta^A$, individuals 6,9,10 and 11 are predicted to be $\beta^S/\beta^S$, and individuals 4,7,8 and 12 are predicted to be $\beta^A/\beta^S$. In each case, the genotype was correctly and unambiguously predicted from the pattern of fragment amplification (see description of FIG. 2 for clinically diagnosed genotype).

The results presented above indicate the potential usefulness of ASPCR for sickle cell diagnosis. The method is rapid and the result is obtained without the use of radioactivity, since all that is required is to visualize the band on a gel using ethidium bromide staining. The technique may be further improved by elimination of the gel separation step. One strategy for this is shown in FIG. 3. As proposed recently by Yamane et al.,[14] the two primers for the PCR reaction could be labeled differently, one with a biotin and one with fluorescent group such as fluorescein or tetramethyl rhodamine. The product of the PCR reaction could be captured on streptavidin-agarose and the presence of the amplified sequence detected with fluorescence. In this case, if one allele specific primer were labeled with one fluorescent group and the other with a different one then the ASPCR could be done simultaneously.

14 Yamane, A., et al., *Nucleic Acids Res.* 20:91 (1988).

The exemplification uses PCR primers that form either an A—A or a T—T mismatch. It is not clear that other mismatches will give equally effective discrimination. As in the case of allele specific oligonucleotide probes, G–T is a likely mismatch to avoid.[15] A competition approach such as that used to improve the discrimination provided by oligonucleotide hybridization probes[16] is contemplated. In this case, a competitive primer is designed which is not able to prime by, for example, including in it a 3' dideoxy or a 3' ribo that has been oxidized. A mixture of a labeled allele specific primer complementary to allele 1 plus an unlabeled priming-defective primer complementary to allele 2 should then allow the specific amplification of allele 1.

15 Kidd, V. J., et al., *Nature* 304:230–234 (1983).
16 Nozari, G., et al., *Gene* 43:23–28 (1986).

ASPCR would appear to work because the priming efficiency with the primer that forms a mismatch at the 3' terminal nucleotide is reduced relative to the priming efficiency of a perfectly matched primer. Since PCR is an exponential process, the yield of amplified product is very sensitive to the efficiency of each round of reaction.[17] It is not known whether the primer forming the mismatch can prime DNA synthesis by removal of the 3' nucleotide by a 3' exonuclease of the DNA polymerase or by utilization of the primer directly. In either case, the yield of product after 25 round of amplification would be much greater for the perfectly matched primer than for the mismatched primer If, for example, the efficiency for no mismatch is 90% and with a mismatch 60%, there would be 73 fold more product produced in the matched primer reaction.[18]

17 Saiki, R. K., et al., *Science* 239:487–491 (1988).
18 Saiki, R. K., et al., *Science* 230:1350–1354 (1985).

The ASPCR is useful in the fields of genetic diagnosis, carrier screening, HLA typing, and any other nucleic acid based diagnostic in which the precise DNA sequence of the priming site is diagnostic for the target. In the case of HLA typing, recent advances have used PCR amplification followed by allele specific oligonucleotide hybridization for the determination of DR, DQ and DP alleles.[19] It should be possible to use ASPCR for the direct analysis of HLA types.

19 Saiki, R. K., et al., *Nature* 324:163–166 (1986); Morel, P. A., et al., *Proc. Natl. Acad. Sci. USA* 85:8111–8115 (1988); Angelini, G., et al., *Human Immunology* 23:77 (1988); Scharf, S., et al., *Human Immunology* 23:143 (1988); Skolnick, M. H., et al., *Genomics* 2:273–279 (1988).

A process for the simultaneous determination of multiple polymorphic loci based on the concept of producing locus-specific amplification products each with a unique length has recently been proposed. In such a system, ASPCR would produce allele specific products, thus permitting the simultaneous analysis of the genotype of the target DNA at multiple loci.

We claim:

1. A method for conducting an allele specific polymerase chain reaction which comprises subjecting DNA which may contain either or both of first and second alleles to a polymerase chain reaction utilizing a primer pair in which one of the primers is complementary to said first allele, but which primer forms a mismatch with said second allele at the 3'-terminal nucleotide of the primer, and utilizing a DNA polymerise wherein said first allele is specifically amplified but little or no amplification of said second allele occurs.

2. A method for conducting an allele specific polymerase chain reaction which comprises subjecting DNA which may contain either or both of first and second alleles to a polymerase chain reaction utilizing a primer pair in which one of the primers is complementary to said first allele, but which primer forms a mismatch with said second allele at the 3'-terminal nucleotide of the primer, and utilizing a *Thermus equaticus* DNA polymerase wherein said first allele is specifically amplified, but little or no amplification of said second allele occurs.

3. A method for diagnosing sickle cell anemia which comprises:
  (a) obtaining a genomic DNA sample from a person;
  (b) subjecting said genomic DNA sample to separate first and second polymerase chain reactions,
  (c) utilizing in said first polymerase chain reaction a first primer set specific to direct amplification of the A→T transversion mutation of the sickle cell allele,
  wherein one primer of said first primer set has a 3'-terminal nucleotide complementary to said transversion mutation, and
  wherein one primer of said first primer set is labelled at its 5'-end with a fluorescent group and the other primer of said first primer set is biotin-labelled at its 5'-end,
  (d) utilizing in said second polymerase chain reaction a second primer set which is specific to direct amplification of the normal allele,
  wherein one primer of said second set has a 3'-terminal nucleotide which is complementary to the normal nucleotide, and said 3'-terminal nucleotide forms a mismatch with. said A→T transversion mutation of the sickle cell allele, and
  wherein on primer of said second primer set is labelled at its 5'-end with a fluorescent group and the other primer of said second primer set is biotin-labelled at its 5'-end,
  (e) passing the polymerase chain reaction amplification products through a streptavidin-agarose column to capture the amplification products which are biotin labelled,
  (f) quantifying said captured amplification products which are labelled with a fluorescent group, by measuring the fluorescence, thereby diagnosing sickle cell anemia if fluorescence is measured in the amplification products of said first or said first and second polymerase chain reactions and not diagnosing sickle cell anemia if fluorescence is measured only in the amplification products of said second polymerase chain reaction.

4. The method of claim 3 wherein said first and second polymerase chain reactions are performed simultaneously and said one primer in each of said first and second primer sets is labelled at its 5'-end with a different fluorescent group.

* * * * *

Disclaimer 5,639,611—R. Bruce Wallace, Greenbrae; Bijay K. Pal, Arcadia; Luis A. Ugozzoli, San Rafael, all of Calif.; Dan Y. Wu, Bellevue, Wash. ALLELE SPECIFIC POLYMERASE CHAIN REACTION. Patent dated June 17, 1997. Disclaimer filed Feb. 15, 2008, by the Assignee, City of Hope, Duarte.

The term of this patent which would extend beyond the expiration date 11 Dec. 2007.

*(Official Gazette March 18, 2008)*